US012790562B2

(12) United States Patent
Gerstmann et al.

(10) Patent No.: US 12,790,562 B2
(45) Date of Patent: Nov. 10, 2026

(54) AROMATIC MONOTHIOKETALS AS FRAGRANCE COMPOUNDS

(71) Applicant: SYMRISE AG, Holzminden (DE)

(72) Inventors: Frank Gerstmann, Frankfurt am Main (DE); Bernd Hoelscher, Halle (DE)

(73) Assignee: SYMRISE AG, Holzminden (DE)

( * ) Notice: Subject to any disclaimer, the term of this patent is extended or adjusted under 35 U.S.C. 154(b) by 800 days.

(21) Appl. No.: 17/768,180

(22) PCT Filed: Oct. 16, 2019

(86) PCT No.: PCT/EP2019/078126

§ 371 (c)(1),
(2) Date: Apr. 11, 2022

(87) PCT Pub. No.: WO2021/073736

PCT Pub. Date: Apr. 22, 2021

(65) Prior Publication Data

US 2024/0117269 A1 Apr. 11, 2024

(51) Int. Cl.

| | |
|---|---|
| ***C11B 9/00*** | (2006.01) |
| ***A61K 8/49*** | (2006.01) |
| ***A61Q 5/02*** | (2006.01) |
| ***A61Q 19/10*** | (2006.01) |
| ***C07D 327/06*** | (2006.01) |

(52) U.S. Cl.

CPC ................ *C11B 9/008* (2013.01); *A61K 8/49* (2013.01); *A61Q 5/02* (2013.01); *A61Q 19/10* (2013.01); *C07D 327/06* (2013.01)

(58) Field of Classification Search

None

See application file for complete search history.

(56) References Cited

U.S. PATENT DOCUMENTS

| | | | | |
|---|---|---|---|---|
| 4,220,561 | A | 9/1980 | Winter et al. | |
| 4,435,315 | A * | 3/1984 | Conrad | C11B 9/0076 424/49 |
| 6,559,109 | B2 | 5/2003 | Lelandais | |
| 8,053,466 | B2 | 11/2011 | Lelandais | |
| 2002/0155960 | A1* | 10/2002 | Lelandais | A23L 27/2052 510/101 |
| 2011/0092604 | A1* | 4/2011 | Wohrle | C11B 9/0084 512/15 |
| 2012/0183490 | A1* | 7/2012 | Chen | A23L 27/2052 424/76.1 |

FOREIGN PATENT DOCUMENTS

| | | | | |
|---|---|---|---|---|
| DE | 25 34 162 | A1 | 2/1976 | |
| GB | 640570 | A | 7/1950 | |
| GB | 645130 | A | 10/1950 | |
| JP | 2009132630 | A | 6/2009 | |
| WO | WO-2009/076792 | A1 | 6/2009 | |
| WO | WO-2011124706 | A1 * | 10/2011 | A23P 10/30 |

OTHER PUBLICATIONS

Choudhury et al., New homologation of 2-hydroxy and 2-mercapto benzylic alcohols, Elsevier (Year: 1997).*

Ndong et al., An efficient and simple one-pot synthesis of 2-perfluoroalkylated benzo[1,3] dioxole derivatives via double-Michael reaction of fluorinated alkynes, May 26, 2018 (Year: 2018).*

Office Action (and English translation) from Chinese Application No. 201980102728.6 dated May 4, 2023.

STN Registry, CAS:254-51-3, 6 pages (1984).

Arctander, "Perfume and Flavor Chemicals," front matter and table of contents, self-publication (1969).

Choudhury et al., "New Homologation of 2-Hydroxy and 2-Mercapto Benzylic Alcohols," Tetrahedron, 53(51):17373-17382 (1997).

* cited by examiner

*Primary Examiner* — Michael G. Hartley

(74) *Attorney, Agent, or Firm* — MARSHALL, GERSTEIN & BORUN LLP

(57) ABSTRACT

The present invention relates to new odorants or odorant mixtures comprising a sensory effective amount of the compounds of formula (I). In addition, the present invention relates to perfume oils, modified perfume oils, perfume compositions, perfume oil preparations and perfumed products comprising at least one of the compounds of formula (I) in a sensory effective amount. Furthermore, the invention relates to the use of at least one of the compounds of formula (I) as an odorant or in odorant mixtures as well as perfumed products.

9 Claims, 1 Drawing Sheet

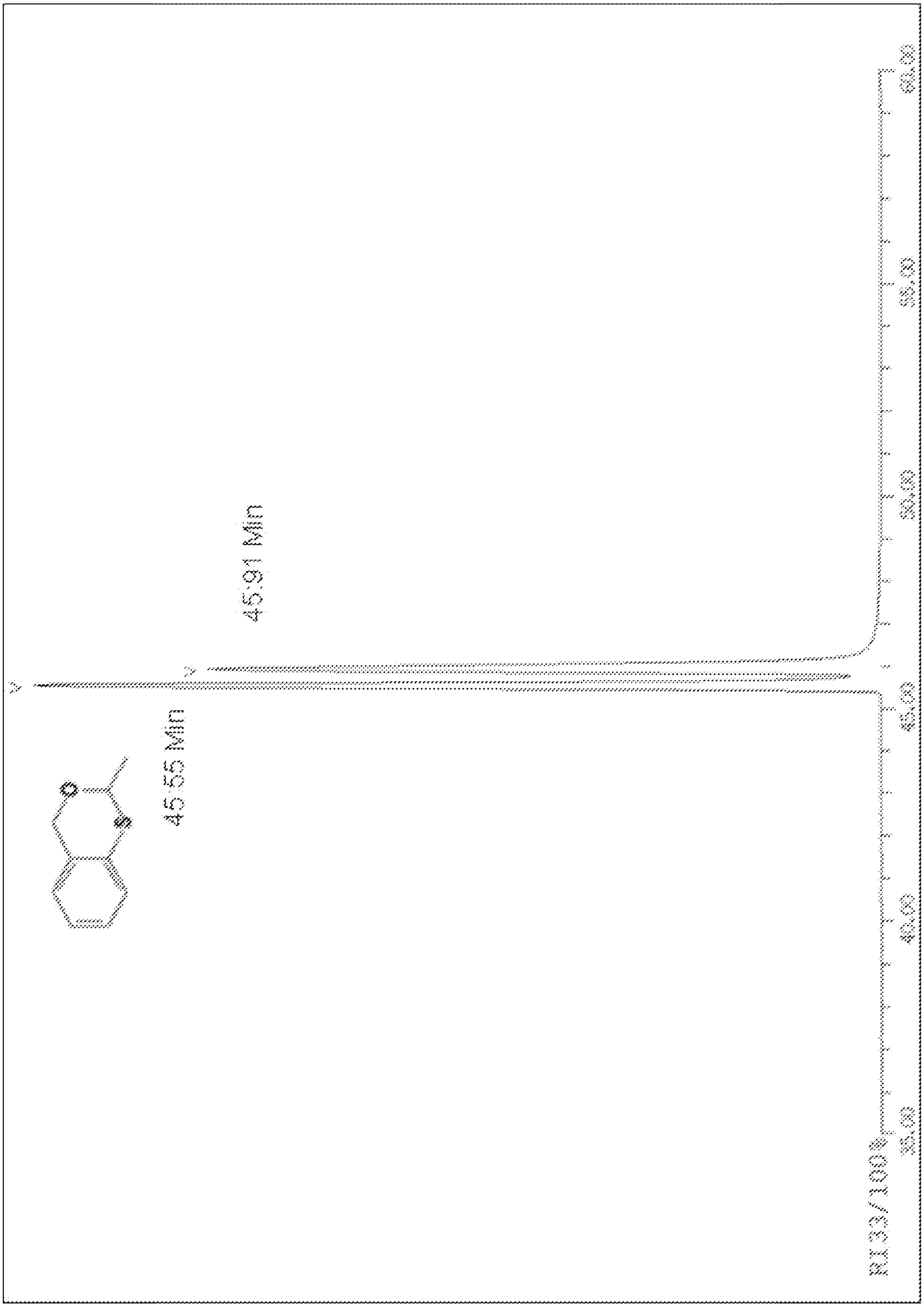
45.91 Min
45.55 Min
35.00
40.00
45.00
50.00
55.00
60.00
RI 33/100%

AROMATIC MONOTHIOKETALS AS FRAGRANCE COMPOUNDS

CROSS-REFERENCE TO RELATED APPLICATIONS

This is a U.S. National Phase of International Application PCT/EP2019/078126, filed Oct. 16, 2019.

FIELD OF INVENTION

The invention relates to odorants or odorant mixtures comprising a sensory effective amount of the compounds of formula (I):

Formula (I)

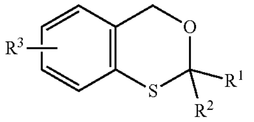

here, $R^1$ and $R^2$ are defined as a hydrogen atom, a linear alkyl group $C_{1-2}$, a linear or branched alkyl group $C_{3-5}$, or a linear or branched alkenyl group $C_{1-5}$. Where the sum of the carbon atoms of $R^1$ and $R^2$ is not more than five carbon atoms. The radical $R^3$ is defined as a hydrogen atom, a linear alkyl group $C_{1-2}$ or a linear or branched alkyl group $C_3$ and may be located at any of the shown four positions of the aromatic ring. The odorant or odorant mixture further comprises the stereoisomers, in particular diastereomers and enantiomers, of the compounds of formula (I) or mixtures thereof. Furthermore, the present invention relates to perfume oils, modified perfume oils, perfume compositions, perfume oil preparations and perfumed products comprising at least one of the compounds of formula (I) in a sensory effective amount. Furthermore, the invention relates to the use of at least one of the compounds of formula (I) as an odorant or in odorant mixtures as well as in perfumed products.

STATE OF THE ART

The aromatic compound indole is a component of a large number of essential oils and perfume oils and is primarily characterized by its odor, which is often perceived as very unpleasant in pure or concentrated form. Used in fine dosages, however, this nitrogenous, organic compound unfolds a fine floral odor that can also be found in jasmine blossom oil, narcissus blossom oil or orange blossom oil and is thus also a component of the odor profile of many flowers.

On the part of perfumery, there is a great demand for floral and leathery odorant, especially notes that have a similar odor profile to indole (S. Arctander, "*Perfume and Flavor Chemicals* (*Aroma Chemicals*)," 2008, Vol. 1, Allured Publishing Corporation) and can be used as components for white floral compositions. Alternatives to indole are also desirable due, on the one hand, to the toxicity of said odorant and, on the other hand, to discoloration problems associated with indole-containing perfume oils, as well as to changes in fragrance due to interactions with other perfume oil components and the photosensitivity of indole. A substitute for indole is, for example, Indoflor®, which has an animalic, floral, leathery and Civet-like odor profile.

However, the search for suitable compounds that circumvent the problems described and thus exhibit positive secondary properties while at the same time revealing a comparable odor profile to indole is proving very difficult due to the large number of possible compounds and the unpredictability of the corresponding odor profile. In addition, it should be possible to mix these odorants well with other compounds, for example other odorants or other components for the production of perfume oils or consumer products, without adversely affecting the olfactory or other functional properties of the odorants or other ingredients.

The 1,3-oxathiane derivatives are known in the literature as odorants (U.S. Pat. Nos. 4,220,561; 6,559,109 B2; 8,053,466 B2) and often exhibit fruity, green and herbaceous notes. An example of a commercialized odorant from this structural class is the odorant Oxanthia (DE 2534162 B2). In all mentioned reports (U.S. Pat. Nos. 4,220,561; 6,559,109 B2; 8,053,466 B2), no aromatic anellated oxathiane are mentioned. Syntheses of aromatically fused oxathianes have already been reported in the literature (M. Yus et al., *Tetrahedron* 1997, 53 (51), 17373; GB 645130 A; GB 640570 A; Q. Wan et al, *Angew. Chem. Int ed.* 2015, 58 (48), 14432). However, none of the literature describes the organoleptic properties of the odorants of the invention, which can be grouped under the general formula (I). In the perfumery field, therefore, aromatically fused oxathiane have not yet found any significant application. In particular, the naming of certain quantity ratios in the production of perfume oils is not known, and a fortiori no olfactory effect is known when combined with other odorants.

The invention is thus based on the general task of providing new odorants that have an animalic and leathery profile and add, enhance or modify floral aspects in fragrance compositions, thus exhibiting fragrance characteristics that go into the indolic.

The present invention is therefore concerned with odorants and odorant mixtures which, to the best of our knowledge, have not been previously reported in the literature and have a comparable odor profile to indole. The present invention is therefore intended to provide odorants or odorant mixtures that exhibit additional positive secondary properties in addition to their positive and characteristic odor properties.

An additional task concerns the reduction or masking of an unpleasant odor and/or the enhancement of positive odor impressions, especially the enhancement of floral, animal, leathery odor impressions by new inventive odorants or mixtures thereof.

A further task relates to the provision of new compounds for use as odorants, preferably mixtures, as well as preparations and consumer goods containing these mixtures and their preparation.

These tasks are solved by the combinations of features defined in the main claims. Preferred embodiments of the present invention are the subject of the subclaims and result from the following description and the embodiment examples.

SUMMARY OF THE INVENTION

A first object of the invention relates to an odorant or an odorant mixture comprising a sensory effective amount of the compounds of formula (I):

Formula (I)

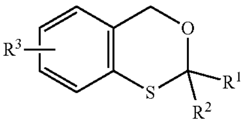

wherein $R^1$ represents a hydrogen atom, a linear alkyl group $C_{1-2}$, a linear or branched alkyl group $C_{3-5}$, or a linear or branched alkenyl group $C_{1-5}$, and $R^2$ represents a hydrogen atom, a linear alkyl group $C_{1-2}$, a linear or branched alkyl group $C_{3-5}$, or a linear or branched alkenyl group $C_{1-5}$, the sum of the carbon atoms of $R^1$ and $R^2$ being not more than five carbon atoms. Further, $R^3$ represents a hydrogen atom, a linear alkyl group $C_{1-2}$, or a linear or branched alkyl group $C_3$, wherein $R^3$ is located at one of the four marked positions of the aromatic ring. The compounds of formula (I) claimed according to the first subject matter further comprise their stereoisomers, in particular diastereomers and enantiomers or mixtures thereof.

In a second object, the present invention comprises a perfume oil comprising or consisting of at least one odorant according to the invention or an odorant mixture according to the invention and one or more additional other odorants.

Third object of the present invention is a modified perfume oil wherein the odorant according to the invention or the odorant mixture according to the invention or the perfume oil according to the invention is microencapsulated, spray-dried, present as inclusion complex or as extrusion product.

In a fourth aspect, the present invention relates to a perfume composition comprising an odorant according to the invention, an odorant mixture according to the invention or a perfume oil according to the invention or a modified perfume oil according to the invention, further comprising at least one supplement, in particular a carrier, and/or at least one additive, in particular at least one formulation adjuvant and/or at least one functional agent.

A further object of the present invention is a perfume oil preparation for a shampoo or a shower gel, which comprises an odorant or an odorant mixture or a perfume oil or a modified perfume oil or a perfume agent according to the invention, as well as further additives suitable for shampoos or shower gels and used in a sensible manner.

Furthermore, in another subject matter, the present invention relates to a perfumed product selected from the group consisting of: detergents, hygiene products, care products, shampoos or shower gels, comprising an odorant or odorant mixture according to the invention, a perfume oil, a modified perfume oil, a perfume composition or a perfume oil preparation.

Finally, in a further aspect, the present invention relates to the use of at least one of the compounds of formula (I) as an odorant or in odorant mixtures, and to the use of at least one of the compounds of formula (I) for reducing or masking an unpleasant odor and/or for enhancing positive odor impressions and/or for enhancing floral, animal or leathery odor impressions.

These and other aspects, features and advantages of the present invention will be apparent to those skilled in the art from a study of the following detailed description and claims. In this regard, any feature from one aspect of the invention may be used or substituted in another aspect of the invention. The examples contained in the present application describe the invention without limiting it. In particular, the present invention is not limited to these examples.

All percentages are by weight unless otherwise stated. Numerical examples given in the form "from x to y" include the values given. When multiple preferred numeric ranges are given in this format, all ranges resulting from the combination of the various endpoints are also included.

Advantageous further embodiments and variants of the invention are given in the dependent claims.

DETAILED DESCRIPTION OF THE INVENTION

In a first aspect, the present invention relates to novel odorants or odorant mixtures comprising a sensory effective amount of the compounds of general formula (I), Formula (I)

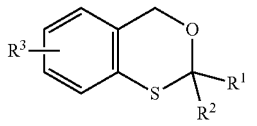

Here, the radicals $R^1$ and $R^2$ are defined as a hydrogen atom, a linear alkyl group $C_{1-2}$, a linear or branched alkyl group $C_{3-5}$ or a linear or branched alkenyl group $C_{1-5}$. The sum of the carbon atoms of $R^1$ and $R^2$ should not exceed five carbon atoms. Furthermore, the radical $R^3$ is defined as a hydrogen atom, a linear alkyl group $C_{1-2}$ or a linear or branched alkyl group $C_3$ and may be located at one of the four highlighted positions of the aromatic ring of the compound of formula (I). The compounds of formula (I) claimed according to the first subject matter further comprise stereoisomers thereof, in particular diastereomers and enantiomers or mixtures thereof.

A preferred embodiment of the present invention therefore relates to compounds of formula (I), in all forms of their positional isomers as well as stereoisomers, in particular their diastereomers and enantiomers, and mixtures thereof.

Particularly preferably, $R^3$ is a hydrogen atom and $R^2$ is also a hydrogen atom and $R^1$ is a methyl group, an isopropyl group or a tert-butyl group.

Furthermore, the radicals $R^1$ and $R^2$ are preferably identical and in this case particularly preferably methyl groups.

The compounds of formula (I) can generally be derived from 1,3-oxathiane. The aromatically fused oxathanes described herein have the basic skeleton of 1,3-oxathiane, to whose ring structure an aromatic six-membered ring is linked via two common carbon atoms, i.e. is fused. Surprisingly, depending on the choice of residues, these compounds have been found to elicit predominantly intense floral fragrances and to exhibit a leathery and animal odor profile.

In perfumery, compounds of formula (I) have not found any significant application so far, especially not in or as odorant or in or as odorant mixtures.

Surprisingly, the odorants and odorant mixtures according to the invention, comprising the compounds of formula (I), exhibit an animal, leathery, floral, fruity and technical odor profile.

The compounds of formula (I) generally represent new strong odorants and/or odorant mixtures, with the odor sensations varying in their subtleties, i.e. in the weighting of the individual notes of the odor profile, from compound to compound, i.e. from odorant to odorant, and from odorant mixture to odorant mixture, respectively.

It has thus surprisingly been found that the odorants or odorant mixtures according to the invention, comprising a sensory effective amount of the compounds of general formula (I), exhibit an intense animalic, leathery odor profile while adding floral aspects to fragrance compositions. Furthermore, the odorants and odorant mixtures according to the invention exhibit high chemical and physical stability and yield as well as a low odor threshold, very good solubility and miscibility with common solvents as well as with other odorants, and a low tendency to react with other odorants, whereby in combination with one or more odorants the olfactory and/or chemical properties of the individual components are not adversely altered. Such changes in odor profiles often result, for example, from the degradation of odorants or from the formation of by-products due to chemical interactions of the individual ingredients with each other, or are due to insufficient stability of the underlying compounds. Another advantage of the compounds according to the invention is their high fragrance intensity at comparatively low concentration. Furthermore, it can be observed that the addition of the odorants or odorant mixtures according to the invention described herein to perfume oil mixtures, gives the compositions significantly more volume and intensity, these appear more balanced and rounded and a distinct and/or complex floral note can be perceived even at low dosages. This low level of use of odorants in the corresponding formulations also ensures that resources are conserved in the manufacture of perfumed products or preparations containing these odorants.

In addition to intensive sensory properties, the compounds of formula (I) described herein also exhibit additional positive secondary properties, such as high stability under certain conditions of use. This stability, particularly in alkaline media such as detergents, hygiene products, care products, shampoos, soaps or shower gels, qualifies such compounds for use and processing in a wide range of applications. Particularly preferred herein is the use of the odorants and odorant mixtures according to the invention in or for the production of shampoos and shower gels. Further preferred is the use of the described odorants and their further developments in detergents, hygiene products, care products, shampoos or shower gels.

In this context, preparations are to be understood as all further developments of the present odorants and odorant mixtures according to the invention as described herein.

In the context of the present invention, the term "compounds of formula (I)" is understood to mean both the individual compounds of formula (I) and all mixtures of the compounds of formula (I) in any mixing ratio. That is, statements in the following description concerning "compounds of formula (I)" apply both to a single compound of formula (I) and to mixtures consisting of or comprising compounds of formula (I) in any mixing ratio.

According to the invention, and preferably, the compounds of the general formula (I) can be present in various forms, corresponding to the possible constitutional isomers (regioisomers) for $R^1$, $R^2$ and $R^3$, as well as stereoisomers of formula (I), both individually and in mixtures. While some of these possible compounds are preferred, as explained below, in principle the invention encompasses all forms of the isomers according to formula (I) as well as mixtures thereof. The invention therefore relates to odorants or odorant mixtures comprising the compounds as such, individually or also mixtures of the compounds according to the invention.

The compounds of formula (I) according to the invention, as defined above, may also be present as stereoisomers. In the context of the present invention, the term stereoisomers includes all possible diastereomers or enantiomers of the compounds of formula (I).

Furthermore, the definition of the compounds of formula (I) also includes mixtures of the stereoisomers, in particular also the racemates or enantiomerically enriched mixtures, as well as their enantiomerically pure forms.

Consequently, the invention relates to the compounds according to the invention corresponding to the general formula (I) as such, individually or also to mixtures of the compounds according to the invention.

By a sensory effective amount is meant a proportion of the compound or compounds of formula (I) which is sufficient to bring about the above effects, i.e. highlighting or emphasizing a pleasant odor note and/or masking or an unpleasant odor note in the odorant mixture. In particular, this is to be understood as a proportion of the compounds of the general formula (I) which is sufficient to evoke a floral, animalic, leathery odor impression, i.e. in which they develop a sensory perceptible effect.

This floral, animalic, leathery odor impression is usually evoked when at least 0.00001% by weight of the compounds of the general formula (I) as described above are present in the odorant or the odorant mixture.

In a preferred further embodiment of the odorant according to the invention or the odorant mixture according to the invention, the radicals $R^1$ and $R^2$ are not the same, with the radicals $R^1$ and $R^2$ preferably differing at least in their isomerism.

In this context, it is further preferred that at least one of $R^1$ or $R^2$ of the compounds of formula (I) represents a hydrogen atom.

Another preferred further embodiment of the present invention relates to compounds of the general formula (I), as well as their stereoisomers, in particular diastereomers and enantiomers, as well as mixtures thereof, wherein the radical $R^1$ represents a hydrogen atom, a methyl or an iso-propyl or tert-butyl group, and the radicals $R^2$ and $R^3$ are each a hydrogen atom. This preferred embodiment can therefore be described by formula (II):

Formula (II)

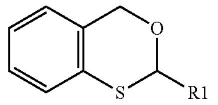

Here, the $R^1$ residue represents a hydrogen atom, a linear alkyl group $C_{1-2}$, a linear or branched alkyl group $C_{3-5}$, or a linear or branched alkenyl group $C_{1-5}$.

Another preferred embodiment of the present invention relates to compounds of formula (I), wherein $R^1$ represents a methyl group and $R^2$ and $R^3$ each represents a hydrogen atom.

A more preferred embodiment of the present invention relates to compounds of formula (I) wherein $R^1$ represents an iso-propyl group and $R^2$ and $R^3$ each represent a hydrogen atom.

An alternative preferred embodiment of the present invention relates to compounds of formula (I) wherein all $R^1$, $R^2$ and $R^3$ are the same, particularly preferably herein $R^1$, $R^2$ and $R^3$ are each hydrogen.

The compounds of formula (II) in the context of the present invention may be present in various forms corresponding to the possible stereoisomers, in particular enantiomers or diastereomers, of formula (II). Therefore, the present invention relates to odorants or odorant mixtures comprising compounds of formula (I), in particular at least one compound of formula (II) or a stereoisomer thereof, as defined above.

Particularly preferred are odorants or odorant mixtures comprising compounds of formula (II) wherein $R^1$ is a methyl group.

Furthermore, the definition of the compounds of formula (II) also includes mixtures of the stereoisomers, in particular also the racemates or enantiomerically enriched mixtures, as well as their enantiomerically pure forms.

In the present text, the term "compounds of formula (II)" covers both the individual compounds and all mixtures of the aforementioned compounds in any mixing ratio.

The term "compounds of formula (I)" thus also covers both the individual compounds selected from the group consisting of the compounds of formula (II) and their stereoisomers, as well as all mixtures of the aforementioned compounds and their stereoisomers in any mixing ratio.

In a preferred embodiment, the present invention relates to an odorant or an odorant mixture comprising a sensory effective amount of the compounds of general formula (I) selected from the group consisting of:

(i) 4H-3,1-benzoxathiin, (ii) 2-methyl-4H-3,1-benzoxathiin, and (iii) 2-Isopropyl-4H-3,1-benzoxathiin.

Particularly preferably, the odorant or odorant mixture according to the invention comprises a sensory effective amount of the compound 2-methyl-4H-3,1-benzoxathiin.

The compounds (i) to (iii) according to the present invention may be present individually, as mixtures, as well as mixtures with the aforementioned compounds of formula (I). The compounds (i), (ii) and (iii) in the context of the present invention may thereby be present in various forms corresponding to the possible stereoisomers, in particular enantiomers or diastereomers.

Surprisingly, these compounds exhibit a leathery-smoky (i), indole-like, cresol-like, and animalic (ii), as well as a salicylate-like, medicinal, fruity, fresh, and Dynascone-like (iii) odor profile, making them suitable for use as odorants and in odorant mixtures as described herein. In addition, they possess positive secondary properties, such as high stability under certain conditions of use. This is particularly critical in the context of combining these odorants or odorant mixtures with other compounds, such as ingredients for the manufacture of consumer products or other odorants.

The compounds of formula (I) according to the invention are excellently suited for use in perfume oils because of their olfactory properties. The compounds can be used as single odorants or combined with a variety of other odorants in numerous products. Particularly advantageously, the odorants and odorant mixtures according to the invention can be combined with other structurally distinguishable odorants in various different proportions to form novel perfume oils.

Therefore, another aspect of the present invention relates to perfume oils comprising at least one odorant according to the invention or an odorant mixture according to the invention and one or more additional other odorants which are not compounds of the general formula (I).

The compounds according to the invention are particularly soluble and/or miscible in other odorants and in a very wide concentration ratio and exhibit a low chemical interaction with other odorants. The odorants or odorant mixtures according to the invention, comprising the compounds of formula (I), have a rounding, balancing effect in these mixtures and improve and intensify the natural underlying olfactory impression, emphasizing in particular the floral fragrance notes. The total mass of the least one compound of formula (I) according to the invention, as defined above, is preferably 0.00001 to 5% by weight, preferably 0.00001 to 1% by weight, and particularly preferably 0.0005 to 0.01% by weight, based on the total weight of the perfume oil.

Particularly preferred proportions according to the invention also result from the explanations described further below and, in particular, from the attached examples.

Surprisingly, the sensory properties of the additional odorant(s) are positively influenced by combination with an effective number of odorants or odorant mixtures according to the invention.

It was also surprising that the compounds of formula (I) of the odorants or odorant mixtures according to the invention can be incorporated permanently and stably into a large number of different formulations, in particular into perfume oils comprising at least one other odorant, without negatively affecting the chemical, physical or olfactory properties of the individual compounds.

It was observed that even low concentrations of the odorants or odorant mixtures according to the invention are sufficient to achieve a significant odor enhancement of the perfume oil compositions.

By using the odorants or odorant substance mixtures of the invention in perfume oils, the sensory properties of the preparation can be modified and, even in low concentrations, evoke the floral, animalic, leathery odor impressions described and measured by experts. Such perfume oils serve the purpose of specifically conveying, modifying or intensifying a desired odor impression, preferably one that is perceived as pleasant or positive in some other way, and possibly creating new interesting odor profiles that are preferably comparable to indolic notes.

Particularly advantageously, the compounds 4H-3,1-benzoxathiin, 2-methyl-4H-3,1-benzoxathiin, 2-isopropyl-4H-3,1-benzoxathiin can be combined in various, different proportions with other odorants to form perfume oils.

Particularly preferred are perfume oils comprising at least a sensory effective amount of the compound 2-methyl-4H-3,1-benzoxathiin, individually, in all forms of its stereoisomers or in mixtures thereof.

Examples of odorants with which the compounds according to the invention can be advantageously combined can be found, for example, in "S. Arctander, "*Perfume and Flavor Chemicals*", Vol. I and II, Montclair, N. J., 1969, self-published" or "H. Surburg and J. Panten, "*Common Fragrance and Flavor Materials",* 5th ed., Wiley-VCH, Weinheim, 2006". In detail, the following extracts from natural raw materials and single odorants are mentioned:

Extracts from natural raw materials selected from the group consisting of:

essential oils, concretes, absolutes, resins, resinoids, balsams, tinctures such as Ambergris oil; Amyris oil; Angelica seed oil; Angelica root oil; Anise oil; Valerian oil; Basil oil; Tree moss absolute; Bay oil; Mugwort oil; Benzoeresin; Bergamot oil; Beeswax absolute; Birch tar oil; Bitter almond oil; Savory oil; Bucco leaf oil; Cabreuva oil; Cade oil; Calmus oil; Camphor oil; Cananga oil; Cardamom oil; Cascarilla oil; Cassia oil; Cassie absolute; Castoreum absolute; Cedar leaf oil; Cedarwood oil; Cistus oil; Citronella oil; Citron oil; Copaiva balsam; Copaiva balsam oil; Coriander oil; Costus root oil; Cumin oil; Cypress oil; Davana oil; Dill herb oil; Dill seed oil; Eau de brouts absolute; Oak moss absolute; Elemi oil; Tarragon oil; Eucalyptus citriodora oil; Eucalyptus oil; Fennel oil; Spruce needle oil; Galbanum oil; Galbanum resin; Geranium oil; Grapefruit oil; Guaiac wood oil; Gurjun balsam; Gurjun balsam oil; Helichrysum absolute; Helichrysum oil; Ginger oil; Iris root absolute; Iris root oil; Jasmine absolute; Calamus oil; Chamomile oil blue; Chamomile oil Roman; Carrot seed oil; Cascarilla oil; Pine needle oil; Curly mint oil; Caraway seed oil; Labdanum oil; Labdanum absolute; Labdanum resin; Lavandin absolute; Lavandin oil; Lavender absolute; Lavender oil; Lemongrass oil; Lovage oil; Lime oil distilled; Lime oil pressed; Linaloe oil; Litsea cubeba oil; Bay leaf oil; Macis oil; Marjoram oil; Mandarin oil; Masso bark oil; Mimosa absolute; Musk grain oil; Musk tincture; Muscat oil; Myrrh absolute; Myrrh oil; Myrtle oil; Clove leaf oil; Clove flower oil; Neroli oil; Olibanum absolute; Olibanum oil; Opopanax oil; Orange flower absolute; Orange oil; Origanum oil; Palmarosa oil; Patchouli oil; Perilla oil; Perubalsam oil; Parsley leaf oil; Parsley seed oil; Petitgrain oil; Peppermint oil; Pepper oil; Allspice oil; Pine oil; Poley oil; Rose absolute; Rose wood oil; Rose oil; Rosemary oil; Sage oil Dalmatian; Sage oil Spanish; Sandal wood oil; Celery seed oil; Spic lavender oil; Star anise oil; Styrax oil; Tagetes oil; Fir needle oil; Tea tree oil; Turpentine oil; Thyme oil; Tolu balsam; Tonka absolute; Tube rose absolute; Vanilla extract; Violet leaf absolute; Verbena oil; Vetiver oil; Juniper berry oil; Wine yeast oil; Wormwood oil; Wintergreen oil; Ylang oil; Hyssop oil; Civet absolute; Cinnamon leaf oil; Cinnamon bark oil, and fractions thereof, or ingredients isolated therefrom;

Individual odorants selected from the groups consisting of:

hydrocarbons, such as 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

aliphatic alcohols, such as hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxy-octan-2-ol; 9-decenol; 10-undecenol; 4-methyl-3-decen-5-ol;

aliphatic aldehydes and their acetals, such as hexanal; heptanal; octanal; nonanal; decanal; undecanal; dodecanal; tridecanal; 2-methyloctanal; 2-methyl nonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undeca dienal; heptanal diethyl acetal; 1,1-dimethoxy-2,2,5-trimethyl-4-hexene; citronellyloxy acetaldehyde; 1-(1-methoxy-propoxy)-(E/Z)-3-hexene;

aliphatic ketones and their oximes, such as 2-heptanone; 2-octanone; 3-octanone; 2-nonanone; 5-methyl-3-heptanone; 5-methyl-3-heptanonoxime; 2,4,4,7-tetramethyl-6-octen-3-one; 6-methyl-5-hepten-2-one;

aliphatic sulfur-containing compounds, such as 3-methylthiohexanol; 3-methyl thiohexyl acetate; 3-mercaptohexanol; 3-mercaptohexyl acetate; 3-mercapto hexyl butyrate; 3-acetylthiohexyl acetate; 1-menth en-8-thiol;

aliphatic nitriles such as 2-nonenoic acid nitrile; 2-undecenoic acid nitrile; 2-tridecene acid nitrile; 3,12-tridecadienoic acid nitrile; 3,7-dimethyl-2,6-octadienoic acid nitrile; 3,7-di methyl-6-octene acid nitrile;

esters of aliphatic carboxylic acids, such as (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxyacetate; methyl 3,7-dimethyl-2,6-octadienoate; 4-methyl-2-pentyl crotonate;

acyclic terpene alcohols, such as citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and their formates, acetates, propionates, isobutyrates, butyrates, isovalerianates, pentanoates, hexanoates, crotonates, tiglinates and 3-methyl-2-butenoates;

acyclic terpene aldehydes and ketones, such as geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethylacetals of geranial, neral, 7-hydroxy-3,7-dimethyloctanal;

cyclic terpene alcohols, such as menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiaol; and their formates, acetates, propionates, isobutyrates, butyrates, isovalerianates, pentanoates, hexanoates, crotonates, tiglinates and 3-methyl-2-butenoates;

cyclic terpene aldehydes and ketones, such as menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-iron; alpha-damascon; beta-damascon; beta-damascenone; delta-damascon; gamma-damascon; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-on; 2-methyl-4-(2,6,6-trimethyl-1-cyclohexen-1-yl)-2-butenal; nootkatone; dihydroneootkatone; 4,6,8-megastigmatrien-3-one; alpha-sinensal; beta-sinensal; acetylated cedarwood oil (methylcedrylketone);

cyclic alcohols, such as 4-tert-butylcyclohexanol; 3,3,5-trimethylcyclohexanol; 3-isocamphylcyclohexanol; 2,6,9-trimethyl-Z2,Z5, E9-cyclododecatrien-1-ol; 2-iso butyl-4-methyl tetrahydro-2H-pyran-4-ol;

cycloaliphatic alcohols, such as alpha,3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclo pent-1-yl)-2-buten-1-ol; 2-ethyl-4-(2,2,3-trimethyl-3-cyclopent-1-yl)-2-buten-1-ol; 3-Methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclo hexyl)hexan-3-ol;

cyclic and cycloaliphatic ethers, such as cineol; cedryl methyl ether; cyclododecyl methyl ether; 1,1-dimethoxycyclododecane; (ethoxymethoxy)-cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

cyclic and macrocyclic ketones, such as 4-tert-butylcyclohexanone; 2,2,5-trimethyl-5-pentylcyclopentanone; 2-heptylcyclopentanone; 2-pentyl cyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopenta decenone; 3-methyl-5-cyclo pentadecenone; 3-methyl-cyclopentadecanone; 4-(1-ethoxy vinyl)-3,3,5,5-tetra methyl cyclohexanone; 4-tert-pentylcyclohexanone; 5-cyclohexa decen-1-one; 6,7-di hydro-1,1,2,3,3-pentamethyl-4(5H)-indanone; 8-cyclohexadecen-1-one; 9-cyclohepta decen-1-one; cyclopentadecanone; cyclohexadecanone;

cycloaliphatic aldehydes, such as 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

cycloaliphatic ketones, such as 1-(3,3-dimethylcyclohexyl)-4-penten-1-on; 2,2-dimethyl-1-(2,4-dimethyl-3-cyclohexen-1-yl)-1-propanon; 1-(5,5-dimethyl-1-cyclohexen-1-yl)-4-penten-1-on; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert-butyl-(2,4-dimethyl-3-cyclohexen-1-yl)ketone;

esters of cyclic alcohols, such as 2-tert-butyl cyclohexyl acetate; 4-tert-butyl cyclohexyl acetate; 2-tert-pentyl cyclohexyl acetate; 4-tert-pentyl cyclohexyl acetate; 3,3,5-trimethyl cyclohexyl acetate; decahydro-2-naphthyl acetate; 2-cyclopentylcyclopentylcrotonat; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5, resp. 6-indenyl acetate; 4,7-methano-3a,4,5,6,7,7a-hexahydro-5, or 6-indenyl propionate; 4,7-methano-3a,4,5,6,7,7a-hexahydro-5, or 6-indenyl isobutyrate; 4,7-methanooctahydro-5, or 6-indenyl acetate;

esters of cycloaliphatic alcohols, such as 1-cyclohexylethyl crotonate;

esters of cycloaliphatic carboxylic acids, such as allyl 3-cyclohexyl propionate; allyl cyclohexyloxy acetate; cis- and trans-methyl dihydro jasmonate; cis- and trans-methyl-jasmonate; methyl 2-hexyl-3-oxocyclopentane carboxylate; ethyl 2-ethyl-6,6-dimethyl-2-cyclohexenecarboxylate; ethyl-2,3,6,6-tetramethyl-2-cyclohexenecarboxylate; ethyl-2-methyl-1,3-dioxolane-2-acetate;

araliphatic alcohols such as benzyl alcohol; 1-phenylethyl alcohol; 2-phenylethyl alcohol; 3-phenyl propanol; 2-phenyl propanol; 2-phenoxyethanol; 2,2-dimethyl-3-phenyl propanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

esters of araliphatic alcohols and aliphatic carboxylic acids, such as benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethyl benzyl acetate; alpha,alpha-dimethylphenyl ethyl acetate; alpha,alpha-dimethylphenyl ethyl butyrate; cinnamyl acetate; 2-phenoxyethyl isobutyrate; 4-methoxybenzyl acetate;

araliphatic ethers, such as 2-phenylethyl methyl ether; 2-phenylethyl isoamyl ether; 2-phenylethyl 1-ethoxyethyl ether; phenylacetaldehyde dimethylacetal; phenyl acet aldehyde diethylacetal; hydratropaaldehyde dimethylacetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

aromatic and araliphatic aldehydes, such as benzaldehyde; phenyl acetaldehyde; 3-phenylpropanal; hydratropaaldehyde; 4-methylbenzaldehyde; 4-methyl phenylacetaldehyde; 3-(4-ethylphenyl)-2,2-dimethylpropanal; 2-methyl-3-(4-isopropyl phenyl) propanal; 2-methyl-3-(4-tert-butylphenyl)propanal; 2-methyl-3-(4-isobutylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

aromatic and araliphatic ketones, such as acetophenone; 4-methyl-aceto phenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,6-hexamethyl-5-indanyl methyl ketone; 6-teabutyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

aromatic and araliphatic carboxylic acids and their esters, e.g. benzoic acid; phenylacetic acid; methyl benzoate; ethyl benzoate; hexyl benzoate; benzyl benzoate; methyl phenyl acetate; ethyl phenyl acetate; geranyl phenyl acetate; phenyl ethyl phenyl acetate; methyl cinnamate; ethyl cinnamate; benzyl cinnamate; phenyl ethyl cinnamate; cinnamyl cinnamate; allylphenoxyacetate; methyl salicylate; isoamyl salicylate; hexyl salicylate; cyclohexyl salicylate; cis-3-hexenyl salicylate; benzyl salicylate; phenyl ethyl salicylate; methyl 2,4-dihydroxy-3,6-dimethylbenzoate; ethyl 3-phenyl glycidate; ethyl 3-methyl-3-phenyl glycidate;

nitrogen-containing aromatic compounds, such as 2,4,6-trinitro-1,3-dimethyl-5-tert-butylbenzene; 3,5-dinitro-2,6-dimethyl-4-tert-butylacetophenone; cinnamic acid nitrile; 3-methyl-5-phenyl-2-pentenoic acid nitrile; 3-methyl-5-phenylpentanoic acid nitrile; methyl anthra nilate; methyl-N-methylanthranilate; schiff'sche bases of methylanthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; scatole; 2-methoxy-3-isopropylpyrazine; 2-isobutyl-3-methoxypyrazine;

phenols, phenyl ethers and phenyl esters, such as tarragol; anethole; eugenol; eugenyl methyl ether; isoeugenol; isoeugenyl methyl ether; thymol; carvacrol; diphenyl ether; beta-naphthyl methyl ether, beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresylphenyl acetate;

heterocyclic compounds, such as 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones, such as 1,4-octanolide; 3-methyl-1,4-octanolide; 1,4-nonanolide; 1,4-deca nolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecene-1,15-olide; cis- and trans-12-pentadecene-1,15-olide; 1,16-hexadecanolide; 9-hexadecene-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin;

as well as any mixtures of the aforementioned odorants.

The compounds according to the invention are readily soluble in a wide variety of solvents. A further embodiment of the present invention therefore further relates to a perfume oil comprising at least one odorant according to the invention or an odorant mixture according to the invention and one or more additional other odorants or perfume oils, and optionally one or more odorless solvents. Preferred solvents which are particularly capable of dissolving the compounds according to the invention are selected from the group consisting of: ethanol, isopropanol, diethylene glycol monoethyl ether, glycerol, propylene glycol, 1,2-butylene glycol, dipropylene glycol, diethyl phthalate, triethyl citrate, isopropyl myristate and mixtures thereof.

The odorants or odorant mixtures according to the invention comprising the compounds of formula (I) form in particular the top note, i.e. those notes whose odor can be perceived particularly quickly, of the perfume oils or preparations containing the odorants or odorant mixtures according to the invention and impart a distinctly more intense and floral character to the compositions. Surprisingly, the olfactory properties of the added odorant or odorants are positively influenced by combination with a sensory effective amount of odorants or odorant mixtures according to the invention. In individual cases, the sensory impression is shifted in the direction of more volume, less dry, more rounded, more balanced, clearly more intense, leathery, floral, animalic and the like. Detailed odor descriptions can be found in the following examples.

A further object of the present invention is a modified perfume oil wherein the odorant according to the invention or the odorant mixture according to the invention or the perfume oil according to the invention is present microencapsulated, spray-dried, as an inclusion complex or as an extrusion product. Preferably, the perfume oil thus modified is added in the form described herein to the (pre)product to be perfumed. Such modification of the perfume oil facilitates both its handling and dosage.

This is particularly advantageous in view of the low concentrations of the odorants or odorant mixtures according to the invention which are required to impart or emphasize a desired odor impression.

Thus, a further embodiment of the present invention preferably relates to a modified perfume oil comprising a perfume oil according to any of the preceding embodiments, wherein the perfume oil is microencapsulated, spray-dried, an inclusion complex or an extrusion product.

In some cases, the properties of perfume oils modified in this way are further optimized by so-called "coating", i.e. covering with suitable materials, with a view to more targeted fragrance release. Preferably, waxy plastics such as polyvinyl alcohol are used for this purpose.

The microencapsulation of the perfume oils according to the invention can be carried out, for example, by the so-called coacervation process using capsule materials made, for example, of polyurethane-like substances or soft gelatin. The spray-dried perfume oils can be prepared, for example, by spray-drying an emulsion, or dispersion, containing the perfume oil, using modified starches, proteins, dextrin and vegetable gums as carriers.

Inclusion complexes can be prepared, for example, by introducing dispersions of the perfume oil and cyclodextrins or urea derivatives into a suitable solvent, such as water.

Extrusion products, on the other hand, can be obtained by fusing the perfume oils with a suitable waxy substance and by extrusion followed by solidification, optionally in a suitable solvent, e.g. isopropanol.

A fourth aspect of the present invention relates to a perfume composition comprising an odorant according to the invention, an odorant mixture, a perfume oil or a modified perfume oil, further comprising at least one supplement, in particular a carrier, and/or at least one additive, in particular at least one formulation adjuvant and/or at least one functional agent.

In a preferred embodiment, the perfume compositions according to the invention comprise synthetic or natural, preferably tasteless and odorless supplements. Such supplements can preferably be solids, particularly preferably carriers, to which the odorant or the odorant mixture or the (modified) perfume oil is adsorbed or else is inserted in the carriers in a (micro)encapsulated form. This ensures both a fine and uniform distribution of the odorants contained in the product and a controlled release of the odorants during use and is therefore particularly suitable for the odorants and odorant mixtures described herein, which already exhibit intense olfactory properties in low concentrations.

Therefore, the perfuming composition according to the invention further preferably comprises a supplementary agent, preferably a carrier agent, wherein the carrier agent comprises one or more substances selected from the group consisting of: porous inorganic materials such as light sulfate, silica gels, zeolites, gypsums, clays, clay granules, aerated concrete, etc., or organic materials such as woods, cellulose-based materials, sugars or plastics such as PVC, polyvinyl acetates or polyurethanes.

Particularly advantageous and therefore preferred in the context of the present invention is a perfuming agent comprising one of the following compounds of formula (I) selected from the group consisting of: 4H-3,1-benzoxathiin, 2-methyl-4H-3,1-benzoxathiin, 2-isopropyl-4H-3,1-benzoxathiin, further comprising a supplement, preferably a carrier, wherein the carrier comprises one or more of the aforementioned substances.

More particularly, the present invention relates to perfume compositions comprising one of the following compounds selected from the group consisting of: 4H-3,1-benzoxathiin, 2-methyl-4H-3,1-benzoxathiin, 2-isopropyl-4H-3,1-benzoxathiin, individually or in mixtures, as well as all forms of the isomers, further comprising a supplement, preferably a carrier, wherein the carrier comprises one or more of the aforementioned substances.

Particularly preferred are perfume compositions comprising at least a sensory effective amount of the compound 2-methyl-4H-3,1-benzoxathiin, individually, in all forms of its stereoisomers or in mixtures thereof.

According to a preferred embodiment of the present invention, in odorants, odorant mixtures or (modified) perfume oils according to the invention, which are used adsorbed on a carrier, the amount of compounds of the formula (I) according to the invention used is usually in a range from 0.00001 to 5 wt. %, preferably 0.00001 to 1 wt. % and particularly preferably 0.0005 to 0.01 wt. %, based on the total odorant or the odorant mixture or the total (modified) perfume oil. %, Another preferred embodiment of the present invention relates to a perfume composition comprising an odorant or an odorant mixture or the (modified) perfume oil comprising the compounds of formula (I) according to the invention, and one or more additives.

A further embodiment of the invention therefore relates to a perfume composition comprising an odorant or an odorant mixture according to the invention or the (modified) perfume oil according to the invention as described above further comprising one or more additives, in particular at least one formulation adjuvant and/or at least one functional agent selected from the group consisting of: preservatives, abrasives, anti-acne agents, anti-aging agents, antibacterial agents, anticellulitis agents, anti-dandruff agents, anti-inflammatory agents, anti-irritant agents, anti-irritant agents, antimicrobial agents, antioxidants, astringents, antiperspirants, antiseptics, antistatics, binders, buffers, carriers, chelating agents, cell stimulants, cleansing agents, conditioning agents, depilatories, surfactants, deodorizers, antiperspirants, emollients, emulsifiers, enzymes, essential oils, fibers, film formers, fixatives, foaming agents, foam stabilizers, anti-foaming substances, foam boosters, fungicides, gelling agents, gel-forming agents, hair care agents, hair shaping agents, hair smoothing agents, moisturizing agents, moistening substances, moisture retaining substances, bleaching agents, strengthening agents, stain removing agents, optical brightening agents, impregnating agents, soil-repellent agents, friction-reducing agents, lubricants, moisturizers, ointments, opacifiers, plasticizing agents, covering agents, polishes, brighteners, polymers, powders, proteins, refatting agents, abrasive agents, silicones, skin soothing agents, skin cleansing agents, skin conditioning agents, skin healing agents, skin whitening agents, skin protecting agents, skin softening agents, cooling agents, skin cooling agents, warming agents, skin warming agents, stabilizers, UV absorbing agents, UV filters, detergents, fabric softeners, suspending agents, skin tanning agents, thickening agents, vitamins, oils, waxes, fats, phospholipids, saturated fatty acids, mono- or polyunsaturated fatty acids, α-hydroxy acids, poly hydroxy fatty acids, liquefiers, dyes, color-protecting agents, pigments, anticorrosives, aromas, flavors, odorants, polyols, surfactants, electrolytes, organic solvents or silicone derivatives.

Such additives usually function as formulation aids and/or functional agents and are used in particular in the manufacture of corresponding consumer goods or perfumed products. Due to the chemical stability of the compounds of formula (I) on which the odorants or odorant mixtures are based, these odorants or odorant mixtures and the perfume oils, modified perfume oils and perfume agents produced therefrom are suitable for use in the manufacture of perfumed products and consumer goods, so that neither the odorants or odorant mixtures or the perfume oils produced therefrom nor the adjuvants and/or additives are negatively affected in their properties.

Further preferred is a perfuming agent comprising one of the following compounds of formula (I) selected from the group consisting of: 4H-3,1-benzoxathiin, 2-methyl-4H-3,1-benzoxathiin, 2-isopropyl-4H-3,1-benzoxathiin, further comprising one or more additives selected from the field of formulation adjuvants and/or functional agents as described above.

In particular, the present invention relates to perfuming compositions comprising one of the following compounds selected from the group consisting of: 4H-3,1-benzoxathiin, 2-methyl-4H-3,1-benzoxathiin, 2-isopropyl-4H-3,1-benzoxathiin, individually or in mixtures, as well as all forms of the isomers, further comprising one or more additives selected from the field of formulation adjuvants and/or functional agents as described above.

Particularly preferred are perfume compositions comprising at least a sensory effective amount of the compound 2-methyl-4H-3,1-benzoxathiin, individually, in all forms of its stereoisomers or in mixtures thereof.

A further embodiment of the present invention further relates to a perfume composition according to the preceding description comprising at least one adjuvant, preferably a carrier comprising one or more substances as described above, as well as at least one additive, in particular at least one formulation adjuvant and/or at least one functional agent as described above.

In this context, it is particularly preferred in the context of the present invention that the perfuming agent comprises at least one of the compounds selected from the group consisting of: 4H-3,1-benzoxathiin, 2-methyl-4H-3,1-benzoxathiin, 2-isopropyl-4H-3,1-benzoxathiin, as well as a supplement, preferably a carrier, and further one or more additives according to the invention.

In particular, the present invention relates to perfume compositions comprising at least one of the following compounds selected from the group consisting of: 4H-3,1-benzoxathiin, 2-methyl-4H-3,1-benzoxathiin, 2-isopropyl-4H-3,1-benzoxathiin, individually or in mixtures as well as all forms of the isomers, further comprising a supplement, preferably a carrier, and further one or more additives according to the invention. Particularly preferred are perfume compositions comprising at least a sensory effective amount of the compound 2-methyl-4H-3,1-benzoxathiin, individually in all forms of its stereoisomers or in mixtures thereof.

Perfumes containing the odorants of the invention or odorant mixtures comprising the compounds of formula (I) must have sufficient chemical and physical stability as such or for the production of consumer goods. To ensure this, it is crucial that the ingredients used do not react adversely with each other. The use of the odorants or odorant mixtures according to the invention is particularly advantageous and preferred due to the low chemical reactivity of the underlying compounds of formula (I), so that neither the odorants or odorant mixtures according to the invention nor the ingredients of the perfumes, perfumed products or consumer goods are adversely altered chemically, physically or olfactorily and thus the physical or physicochemical properties thereof are not adversely affected. This is due in particular to the low concentration of the amount of the compounds of formula (I) used, which is required to achieve an intense odor profile in accordance with the invention.

A further aspect of the present invention relates to perfume oil preparation for a shampoo or shower gel comprising an odorant according to the invention or an odorant mixture according to the invention, a perfume oil according to the invention, a modified perfume oil according to the invention or a perfume agent according to the invention according to one of the aspects or objects according to the invention mentioned above, further comprising additives suitable for shampoos or shower gels and used in a sensible manner. Such additives may further be selected from the foregoing list of descriptive formulation adjuvants and/or functional agents suitable for use in shampoos and/or shower gels.

The compounds of the invention to be used in odorants or odorant mixtures, as defined above, and the mixtures thereof, as well as the (modified) perfume oils, perfume compositions and perfume oil preparations of the invention, as defined above, are used in particular for the production of perfumed products.

Accordingly, a sixth object of the present invention describes perfumed products selected from the group consisting of: detergents, hygiene products, personal care products, shampoos or shower gels comprising an odorant or an odorant mixture, a perfume oil, a modified perfume oil, a perfume composition or a perfume oil preparation according to any of the preceding aspects and definitions. A perfumed product or consumer product according to the invention comprising the compounds according to the invention as defined above, preferably in a sensory effective amount.

Since such products often have a large number of chemical ingredients, it is important that the odorants used or their preparations also have a low chemical reactivity in order to counteract undesirable interactions or decompositions. The use of the compounds according to the invention is therefore particularly advantageous since they exhibit low reactivity and high stability, so that neither the compounds according to the invention nor the ingredients of the consumer goods or perfumed products are adversely altered. In this context, particular emphasis should be placed on the low concentration of the odorants which is necessary to achieve the desired fragrance effect, which avoids any adverse change in the properties of the perfumed products or their other ingredients.

The invention also relates to the use of the compounds according to the invention. Therefore, the present invention further relates to the use of a compound of formula (I) according to the invention as odorant or odorant mixture.

Particularly preferred in this context is the use of the above-described compounds of the formulae (II), and preferably compounds (i) to (iii) or a stereoisomer thereof, or a mixture of the above-mentioned compounds or stereoisomers thereof as odorant or odorant mixtures.

The odorants and odorant mixtures described herein, comprising a sensory effective amount of the compounds of formula (I), are readily available or preparable, exhibit high olfactory intensity even in low concentration, are chemically inert to other odorants, whereby in combination with one or more odorant(s) the odor profile is not adversely altered, and possess high stability in various mixtures or preparations. Therefore, these compounds are excellently suited as or in odorant(s) or odorant mixture(s) as well as their use in preparations comprising these odorant(s) or odorant mixture(s).

In particular, the present invention relates to the use of one of the following compounds selected from the group consisting of: 4H-3,1-benzoxathiin, 2-methyl-4H-3,1-benzoxathiin, 2-isopropyl-4H-3,1-benzoxathiin, individually or in mixtures, as well as all forms of the isomers, as an odorant or odorant mixture. Particularly preferred is the use of the compound 2-methyl-4H-3,1-benzoxathiin, individually in all forms of its stereoisomers or in mixtures thereof.

Furthermore, the present invention relates to the use of at least one of the compounds of formula (I) according to any of the preceding aspects for reducing or masking an unpleasant odor and/or for enhancing positive odor impressions and/or for enhancing floral, animal, leathery odor impressions. Amplify in this context means to highlight or emphasize a particular odor note.

More particularly, the present invention relates to the use of odorants or odorant mixtures comprising compounds selected from the group consisting of: 4H-3,1-benzoxathiin, 2-methyl-4H-3,1-benzoxathiin, 2-isopropyl-4H-3,1-benzoxathiin, individually or in mixtures, as well as all forms of the isomers for reducing or masking an unpleasant odor and/or for enhancing positive odor impressions and/or for enhancing floral, animal, leathery odor impressions. Particularly preferred in this context is the use of 2-methyl-4H-3,1-benzoxathiin.

With respect to the terms "highlight" or "emphasize," in the context of the present application, it is understood to mean an enhancement of the intensity of a positive, pleasant odor, particularly odors or odor notes of the floral type.

Since floral odorants, i.e. odorants with a floral note, are particularly preferred in the perfumery industry, the odorants and odorant mixtures described in the present invention and compositions resulting therefrom comprising the compounds of formula (I) are particularly suitable for such uses. It should be noted that reducing or masking an unpleasant odor is a major challenge on the part of perfumers, and the unpleasant odor impressions can usually only be masked with the aid of substantial amounts of pleasantly scented odorants. Therefore, a high-quality odorant or odorant mixture is characterized by the fact that the aforementioned odorants or odorant blends reduce or mask unpleasant odors, while at the same time highlighting positive olfactory impressions.

The preparations described herein comprising at least one of the compounds of formula (I) show a significant enhancement of the floral, animalic and leathery fragrance notes already at low dosages and are excellently suited for such use due to this and in particular due to the high fragrance intensity, i.e. high efficacy in low concentration.

As a result, in the context of the present invention, for example, both an unpleasant odor note of a particular (unpleasant-smelling) substance can be masked or reduced, and a pleasant odor note of the same (also pleasant-smelling) substance can be enhanced.

In addition, the odorants and odorant mixtures according to the invention, as well as compositions containing these odorants or odorant mixtures, can be used to round off, balance and intensify the odor properties of perfume oils and consumer products containing the above.

Finally, the present invention relates to the use of the odorants or odorant mixtures, perfume oils, modified perfume oils or perfume oil preparations according to the invention, comprising compounds of formula (I), in concentrated form, in solutions or in other modified form for the production of consumer goods or perfumed products in the sense of the invention such as. e.g. perfume extracts, eau de parfums, eau de toilettes, shaving waters, eau de colognes, pre-shave products, splash colognes and perfumed refreshing wipes, as well as for the perfuming of acidic, alkaline and neutral cleaning agents, e.g. floor cleaners, window glass cleaners, dishwashing detergents, bathroom and sanitary cleaners, scouring milks, solid and liquid WC cleaners, powder and foam carpet cleaners, liquid laundry detergents, powder laundry detergents, laundry pre-treatment agents such as bleaches, softeners and stain removers, laundry softeners, laundry soaps, laundry tablets, disinfectants, surface disinfectants, as well as air fresheners in liquid, gel or solid form, aerosol sprays, waxes and polishes such as furniture polishes, floor waxes, shoe polishes, and personal care products such as solid and liquid soaps, shower gels, shampoos, shaving soaps, shaving foams, bath oils, cosmetic emulsions of the oil-in-water, water-in-oil and water-in-oil-in-water types, such as skin creams and lotions, face creams and lotions, sun creams and lotions, after-sun creams and lotions, hand creams and lotions, foot creams and lotions, depilatory creams and lotions, after-shave creams and lotions, tanning creams and lotions, hair care products such as hair sprays, hair gels, hair lotions, hair conditioners, permanent and semi-permanent hair dyes, hair shaping products such as cold waves and hair straighteners, hair tonics, hair creams and lotions, deodorants and antiperspirants such as underarm sprays, roll-ons, deodorant sticks, deodorant creams or decorative cosmetic products.

Particularly preferred in this context is the use of odorants or odorant mixtures, (modified) perfume oils, perfume compositions or perfume oil preparations comprising one of the following compounds selected from the group consisting of: 4H-3,1-benzoxathiin, 2-methyl-4H-3,1-benzoxathiin, 2-isopropyl-4H-3,1-benzoxathiin. Particularly preferred in this context are odorants or odorant mixtures, (modified) perfume oils, perfume compositions or perfume oil preparations comprising 2-methyl-4H-3,1-benzoxathiin.

EXAMPLES

The present invention is described in more detail below with reference to examples of embodiments. First, the examples given relate to the preparation of compounds of the general formula (I) and particularly preferred compounds. Furthermore, it should be noted that the IUPAC nomenclature may differ from the generic name used so far.

For spectroscopic data, the following English-language regulation applies with regard to the use of dots as separators for numerical data in order to ensure better clarity of the measurement results. In this context, in data of the form "δ=7.12 (dd, J=3.7, 0.9 Hz, 2H)" the measured values are to be read as "δ=7.12", "3.7" and "0.9".

General Process for the Preparation of the Compounds of Formula (I)

In the following, different preparation methods for the synthesis of the oxathiane of general formula (I) starting from compounds of formula (Ill), are described.

As will be explained in more detail below, the compounds of the invention of the general formula (I), and thus also of the formula (II), can be prepared by a process which comprises at least steps (i) and (ii). For this purpose, the corresponding thiosalicylic acid (Ill) is assumed:

Here, the radicals R1 and R2 are defined as a hydrogen atom, a linear alkyl group C1-2, a linear or branched alkyl group $C_3$-5 or a linear or branched alkenyl group C1-5. In sum, R1 and R2 should not carry more than a total of five carbon atoms. The R3 radical is defined as a hydrogen atom, a linear alkyl group C1-2 or a linear or branched alkyl group C3 and may be located at any of the four highlighted positions of the aromatic ring of the corresponding compound. The odorant or odorant mixture claimed according to the invention, comprising a sensory effective amount of the compounds of formula (I) are present as various regioisomers and/or stereoisomers according to the invention, in particular diastereomers and enantiomers, or mixtures thereof.

In a first step (i), the compounds (III) are reduced to the corresponding benzyl alcohol (IV). Common reducing agents can be used for this purpose. Particularly preferred is the reducing agent lithium aluminum hydride in tetrahydrofuran (THF).

In a second step (ii), the alcohols (IV) are acid-condensed to give the compounds of formula (I) according to the invention. This is carried out under standard reaction conditions in the acid. Particularly preferred in this step is the use of a Dean-Stark apparatus with separation of the condensate.

Another alternative access route to the compounds of general formula (I) according to the invention is via the formation of the corresponding lactone (V) (in analogy to the process described in patent specification JP 2009132630 A) (step iii) and a subsequent homogeneous hydrogenation to the corresponding benzyl alcohol (IV) (step iv). Via this preferred reaction path, the use of the hazardous substance lithium aluminum hydride can be avoided.

In a third step (ii), the alcohols (IV) are acid-condensed to give the compounds of formula (I) according to the invention. This is carried out under standard reaction conditions in the acid. Particularly preferred in this step is also the use of a Dean-Stark apparatus with separation of the condensate.

The invention is described below with reference to examples of embodiments. As will be explained in more detail below, the compounds of formula (I) according to the invention can be synthesized in the following manner described below.

The starting material (2-sulfanylphenyl)methanol (corresponding to compounds of formula (IV)) was prepared following the prescription of R. C. Hartley et al. (R. C. Hartley et al., *J. Org. Chem.* 2004, 69 (18), 6145).

It was found that the conversion in step (ii) of compounds of formula (IV) to compounds of formula (I) proceeds

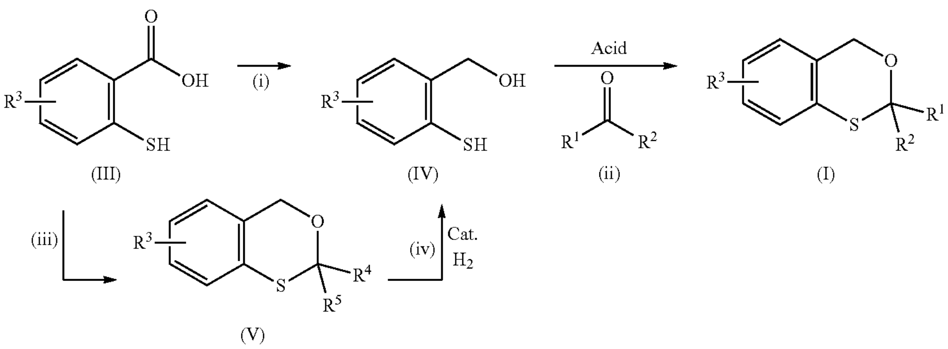

(III) (IV) (I) (V)

particularly well, i.e. in particular with high yield and in a short period of time, in the presence of sulfonic acids.

Synthesis Procedure for the Preparation of Benzoxathianes of the General Formula (I)

At the water separator and under nitrogen, the carbonyl component (2.0-3.0 eq.) is introduced and dissolved in toluene. (2-Sulfanylphenyl)methanol (1.0 eq.) is then added at room temperature and acidified with methanesulfonic acid (0.01-0.1 eq.). The reaction mixture is then heated to reflux until complete conversion. After the reaction is complete, the reaction solution is cooled to room temperature, diluted with methyl tert-butyl ether, and carefully washed with a saturated sodium bicarbonate solution. The phases are separated and the organic is washed with distilled water. The separated organic phase obtained in this way is then dried over sodium sulfate, filtered and freed from solvent in vacuo. The crude product, benzoxathiane, is subjected to distillative purification or chromatographic purification.

Preparation Example 1

Synthesis of 4H-3,1-benzoxathiin

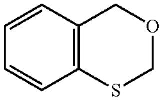

Following the synthesis procedure, 191.96 g (1.37 mol) (2-sulfanylphenyl)methanol and 86.56 g paraformaldehyde were reacted in the presence of 2.60 g (13.69 mmol) para-toluenesulfonic acid monohydrate. The crude product was distilled (3 mbar, bp. 95° C.) over a packed column (a length of 40 cm). 43.7 g (227 mmol, purity 99.5%, yield 21%) of 4H-3,1-benzoxathiin was obtained.

Spectroscopic data of 4H-3,1-benzoxathiin:

EI-MS m/z (%): 152 (53, $[M]^+$), 122 (100), 108 (1), 95 (1), 89 (3), 78 (27), 69 (5), 63 (5), 51 (7), 45 (6), 39 (5), 29 (1).

$^1$H NMR (400 MHz, $CDCl_3$, 300K): δ=7.12 (dd, J=3.7, 0.9 Hz, 2H), 7.07 (ddd, J=7.5, 4.8, 3.9 Hz, 1H), 6.95 (dp, J=7.5, 0.9 Hz, 1H), 5.09 (s, 2H), 4.88 (d, J=0.9 Hz, 2H) ppm.

$^{13}$C-NMR (101 MHz, $CDCl_3$, 300K): δ=131.17, 130.26, 127.91, 127.14, 126.07, 124.89, 69.10, 68.89 ppm.

Odor description of 4H-3,1-benzoxathiin: leather, smoke.

Example 2

Synthesis of 2-methyl-4H-3,1-benzoxathiin

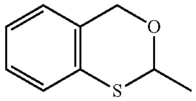

Following the synthesis procedure, 295.82 g (2.11 mol) (2-sulfanylphenyl)methanol and 501.75 g (4.23 mol) acetaldehyde diethyl acetal were reacted in the presence of 2.02 g (0.02 mol) methanesulfonic acid and 145 mL toluene. The crude product was distilled over a packed column (45 cm) (28 mbar, bp. 156° C.). 273.55 g (1.64 mol, purity 99.4%, yield 78%) of 2-methyl-4H-3,1-benzoxathiin was obtained.

Spectroscopic data of 2-methyl-4H-3,1-benzoxathiin:

EI-MS m/z (%): 166 (34, $[M]^+$), 122 (100), 109 (1), 89 (3), 78 (27), 69 (5), 63 (5), 51 (6), 45 (5), 39 (5), 29 (1).

$^1$H NMR (400 MHz, $CDCl_3$, 300K): δ=7.16-7.02 (m, 3H), 6.96 (dq, J=7.6, 0.8 Hz, 1H), 5.26 (q, J=6.1 Hz, 1H), 4.96 (d, J=15.7 Hz, 1H), 4.91 (d, J=15.7 Hz, 1H), 1.64 (d, J=6.1 Hz, 3H) ppm.

$^{13}$C-NMR (101 MHz, $CDCl_3$, 300K): δ=131.99, 129.36, 127.31, 127.23, 125.74, 124.57, 77.70, 69.92, 21.84 ppm.

Mass spectroscopic analysis was performed using an Agilent MSD 5973 N series mass spectrometer and the following parameters.

Ionization: EI+;

Temperatures: ion source: 230° C., transfer line: 230° C.;

Mass range: 25-300 (full scan); and

Ionization energy: 70 eV.

Odor description of 2-methyl-4H-3,1-benzoxathiin: Indole-like, cresol-like, animal-like.

FIG. 1 shows the GC sniff of a chiral column of 2-methyl-4H-3,1-benzoxathiin. The following parameters were selected for the measurement in an Agilent 6890 A series gas chromatograph:

Column: 25 m Hydrodex-g-TBDAc, inner diameter 0.25 mm, film thickness, 0.25 μm; Temperature program: start 40° C., rate 2° C./min, end 180° C.;

Carrier gas: helium 1.8 ml/min, column pressure 2.077 bar, split 10; and

Injector: KAS 4, injection temperature 40° C., rate 12° C./sec, end 180° C. (hold for 5 minutes).

The measurement (FIG. 1) shows the presence of both chiral compounds of 2-methyl-4H-3,1-benzoxathiin. Both compounds exhibit basically the same odor profile, although the rear compound has a more intense odor. The odor profile can be described as strong, tart, animalic and indole-like.

Preparation Example 3

Synthesis of 2-isopropyl-4H-3,1-benzoxathiin

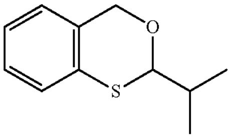

Following the synthesis procedure, 2.00 g (14.26 mmol) (2-sulfanylphenyl)methanol and 3.09 g (42.78 mmol) isobutyraldehyde were reacted in the presence of 272 mg (1.43 mmol) para-toluenesulfonic acid monohydrate and 26 mL toluene. The crude product was distilled over a ball tube (1.1 mbar, bp. 125° C.). 2.16 g (11.12 mmol, purity 99.3%, yield 78%) of 2-isopropyl-4H-3,1-benzoxathiin was obtained.

Spectroscopic data of 2-isopropyl-4H-3,1-benzoxathiin:

EI-MS m/z (%): 194 (23, $[M]^+$), 151 (14), 122 (100), 109 (1), 89 (2), 78 (18), 71 (4), 63 (2), 51 (2), 45 (8), 43 (6), 39 (4), 27 (3).

$^1$H NMR (400 MHz, $CDCl_3$, 300K): δ=7.09 (dd, J=3.7, 0.9 Hz, 2H), 7.01 (dt, J=7.5, 4.0 Hz, 1H), 6.94 (dt, J=7.5, 1.1 Hz, 1H), 4.96 (d, J=5.9 Hz, 1H), 4.90 (dd,

J=14.7, 0.8 Hz, 1H), 4.89 (dd, J=15.0, 0.9 Hz, 1H), 2.09 (hept, J=6.8, 5.8 Hz, 1H), 1.08 (d, J=6.8 Hz, 3H), 1.06 (d, J=6.8 Hz, 3H) ppm.

$^{13}$C-NMR (101 MHz, $CDCl_3$, 300K): δ=132.29, 129.96, 127.72, 127.20, 125.67, 124.38, 87.74, 77.22, 70.35, 33.76, 18.22, 18.07 ppm.

Odor description of 2-isopropyl-4H-3,1-benzoxathiin: salicylate-like, medicinal, fruity, fresh, Dynascone-like.

Preparation Example 4

Synthesis of 2-tert-butyl-4H-3,1-benzoxathiin

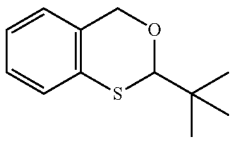

Following the synthesis procedure, 2.45 g (17.50 mmol) (2-sulfanylphenyl)methanol and 4.52 g (52.50 mmol) pivalinaldehyde were reacted in the presence of 334 mg (1.75 mmol) para-toluenesulfonic acid monohydrate and 32 mL toluene. The crude product was distilled over a ball tube (3 mbar, bp. 165° C.). 2.36 g (11.19 mmol, purity 98.5%, yield 64%) of 2-tert-butyl-4H-3,1-benzoxathiin was obtained.

Spectroscopic data of 2-tert-butyl-4H-3,1-benzoxathiin:

EI-MS m/z (%): 208 (23, $[M]^+$), 151 (37), 122 (100), 109 (1), 91 (2), 78 (16), 71 (3), 63 (2), 57 (14), 51 (3), 45 (8), 41 (6), 39 (4), 29 (5).

$^1$H NMR (400 MHz, $CDCl_3$, 300K): δ=7.10 (d, J=3.0 Hz, 2H), 7.06-6.99 (m, 1H), 6.97-6.93 (m, 1H), 4.94 (d, J=14.9 Hz, 1H), 4.93 (s, 1H), 4.87 (d, J=14.8 Hz, 1H), 1.08 (s, 9H) ppm.

$^{13}$C-NMR (101 MHz, $CDCl_3$, 300K): δ=132.60, 130.00, 127.83, 127.15, 125.59, 124.26, 91.40, 70.82, 35.94, 25.69 ppm.

Odor description of 2-tert-butyl-4H-3,1-benzoxathiin: Technical.

Preparation Example 5

Synthesis of 2,2-dimethyl-4H-3,1-benzoxathiin

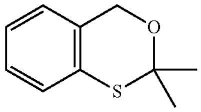

Following the synthesis procedure, 2.45 g (17.50 mmol) (2-sulfanylphenyl)methanol and 3.05 g (52.50 mmol) acetone were reacted in the presence of 334 mg (1.75 mmol) methanesulfonic acid and 32 mL toluene. The crude product was purified by column chromatography on silica gel (cyclohexane/acetic ester=97:3). 0.99 g (5.49 mmol, purity 99.2%, yield 31%) of 2,2-dimethyl-4H-3,1-benzoxathiin was obtained.

Spectroscopic data of 2,2-dimethyl-4H-3,1-benzoxathiin:

EI-MS m/z (%): 180 (19, $[M]^+$), 122 (100), 109 (1), 91 (2), 89 (1), 78 (19), 69 (3), 63 (2), 51 (3), 43 (5), 39 (4), 27 (1).

$^1$H NMR (400 MHz, $CDCl_3$, 300K): δ=7.18-7.15 (m, 1H), 7.13 (dd, J=4.8, 1.9 Hz, 1H), 7.07 (d, J=1.7 Hz, 1H), 7.07-7.03 (m, 1H), 4.88 (s, 2H), 1.68 (s, 6H) ppm.

$^{13}$C NMR (101 MHz, $CDCl_3$, 300K): δ=206.99, 192.78, 191.80, 191.67, 163.50, 133.88, 132.25, 132.13, 131.98, 130.04, 129.15, 128.86, 128.60, 128.56, 127.95, 127.26, 126.32, 125.51, 124.50, 123.52, 86.16, 82.02, 70.23, 64.25, 63.17, 63.15, 30.92, 29.47, 29.12 ppm.

Odor description of 2,2-dimethyl-4H-3,1-benzoxathiin: Technical.

Application Examples

TABLE 1

Overview of the new odorants and their perfumery characterization:

| Structure | Smell |
|---|---|
| 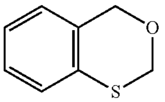 | Leather, smoke |
| 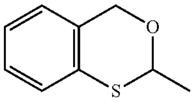 | Indole-like, cresol-like, animal-like |
| 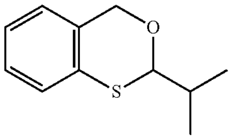 | Salicylate-like, medicinal, fruity, fresh, Dynascone-like. |
| 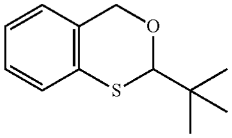 | Technical |
| 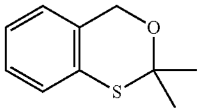 | Technical |

The odor perception threshold, i.e. the ODT value ("odor detection threshold"), was determined using a dynamic olfactometer designated TO8 and a group of experts in accordance with the EN 13725 standard, in which an odorous air sample is diluted with clean air. The dilution is presented to the test persons (testers) for evaluation. The odor description was carried out by a group of experts comprising 10 members.

TABLE 2

ODT values of 2-methyl-4H-3,1-benzoxathiin and 4H-3,1-benzoxathiin in air:

| Odorant | ODT value |
|---|---|
| 2-methyl-4H-3,1-benzoxathiin | 3.6 ng/L |
| 4H-3,1-benzoxathiin | 43.6 ng/L |

As the results of the olfactometric evaluation show, both compounds exhibit a clearly perceptible odor. However, the odor threshold value of 2-methyl-4H-3,1-benzoxathiin is significantly lower, which means that this compound is perceived more quickly and more intensively by the test subjects. Due to the lower odor threshold value, even smaller dosing quantities of the odorants or odorant mixtures are sufficient to produce a perceptible odor.

Thus, even small amounts of the odorants or odorant mixtures according to the invention are excellently suited for generating and evoking the odor impressions on which it is based.

Thus, the compounds of formula (I) are also eminently suitable for reducing or masking an unpleasant odor and/or for enhancing positive odor impressions and/or for intensifying floral, animal or leathery odor impressions.

Example of Embodiment 1

Perfume Oil Composition I (Perfume Oil I)

The following specified perfume oil can be used to perfume eau de toilettes.

TABLE 3

| Composition of perfume oil composition I: | |
|---|---|
| Odorant | Weight (mg) |
| CASTOREUM GIVCO 116/6 | 5 |
| CISTUS LABDANUM ABS. SIS 10% DPG | 50 |
| CIVET 394AB TYPE BASE | 2 |
| DIPROPYLENE GLYCOL | 562 |
| IRALDEIN BETA COEUR | 100 |
| ISO E SUPER | 100 |
| ISOBUTYLQUINOLINE 10% DPG | 24 |
| MUSCONE | 1 |
| PHENYLACETIC ACID 10% DPG | 1 |
| STYRAX RESIN CLAIR | 50 |
| STYRAXOEL PYROGENS | 100 |

The perfume oil prepared was divided into two equal parts. To eliminate dilution effects, a first part of the perfume oil was mixed with 0.5% by weight of dipropylene glycol (DPG), based on the total amount of the first part of the perfume oil. To the second part of the perfume oil, 0.5 wt % 4H-3,1-benzoxathiin 10% DPG was added (i.e., a 10% solution of 4H-3,1-benzoxathiin in DPG), based on the total amount of the part of the perfume oil. The resulting compositions were olfactorily compared with each other.

According to perfumers, the addition of 0.5% by weight 4H-3,1-benzoxathiin 10% DPG gives the composition more volume and a soft leather note. This makes the smell less dry and perceived as more rounded.

Execution Example 2

Perfume Oil Composition II (Perfume Oil II)

The following specified perfume oil can be used to perfume soap.

TABLE 4

| Composition of perfume oil composition II: | |
|---|---|
| Odorant | Weight [mg] |
| ALDEHYDE C14 SOG | 15 |
| AURANTIOL 50% DPG | 20 |
| BENZYL ACETATE | 120 |

TABLE 4-continued

| Composition of perfume oil composition II: | |
|---|---|
| Odorant | Weight [mg] |
| BENZYL SALICYLATE | 120 |
| CINNAMYL ACETATE | 15 |
| CITRONELLYL ACETATE EXTRA | 10 |
| DIPROPYLENE GLYCOL | 2 |
| DODECALACTONE DELTA | 10 |
| ETHYLENE BRASSYLATE | 60 |
| ETHYLMALTOL 10% DPG | 5 |
| ETHYL VANILLIN 10% DPG | 5 |
| EUGENOL NAT. | 2 |
| FLORAZON | 1 |
| GERANYL ACETATE PURE | 25 |
| GLOBALIDE ® | 10 |
| HEDION | 90 |
| HEXENYL SALICYLATE CIS-3 | 5 |
| HEXYL CINNAMALDEHYDE ALPHA | 150 |
| INDOFLOR ® CRYST. | 2 |
| ISOEUGENOL | 1 |
| JASMINE LACTONE 10% DPG | 5 |
| JASMON CIS | 1 |
| JAVANOL 10% DPG | 5 |
| CRESOL METHYL ETHER PARA | 5 |
| LACTOJASMONE | 10 |
| LINALOOL | 200 |
| METHYL ANTHRANILATE | 5 |
| METHYLBENZOAT | 15 |
| METHYL SALICYLATE PF | 5 |
| OCTALACTONE GAMMA | 30 |
| ORYCLON SPECIAL | 30 |
| PRENYL ACETATE | 5 |
| PROPENYLGUETHOL | 1 |
| SANJINOL | 15 |

The perfume oil prepared was divided into two equal parts. To eliminate dilution effects, a first part of the perfume oil was spiked with 0.1 wt. % dipropylene glycol (DPG), based on the total amount of the first part of the perfume oil. To the second part of the perfume oil, 0.1 wt. % 4H-3,1-benzoxathiin 10% DPG was added (i.e., a 10% solution of 4H-3,1-benzoxathiin in DPG), based on the total amount of the part of the perfume oil. The resulting compositions were olfactorily compared with each other.

According to perfumers, the addition of 0.1% by weight of 4H-3,1-benzoxathiin 10% DPG gives the composition a strong floral complexity. In particular, tuberose notes stand out, which perfectly balance the overall composition.

Example of Execution 3

Perfume Oil Composition III (Perfume Oil III)

The following specified perfume oil can be used to perfume shampoos and shower gels.

TABLE 5

| Composition of perfume oil composition III: | |
|---|---|
| Odorant | Weight [mg] |
| ALDEHYDE C18 SOG. | 5 |
| BENZYL ACETATE | 50 |
| BENZYL SALICYLATE | 200 |
| CALONE FF 10% DPG | 5 |
| FLOROSA | 200 |
| HEDION | 300 |
| ISORALDEIN 70 | 20 |
| LINALOOL | 150 |
| METHYL ANTHRANILATE | 5 |
| ORANGENOEL | 20 |
| VANILLIN | 10 |

The perfume oil prepared was divided into two equal parts. To eliminate dilution effects, a first part of the perfume oil was mixed with 2.5% by weight of dipropylene glycol (DPG), based on the total amount of the first part of the perfume oil. To the second part of the perfume oil, 2.5 wt. % 4H-3,1-benzoxathiin 10% DPG was added (i.e., a 10% solution of 4H-3,1-benzoxathiin in DPG), based on the total amount of the part of the perfume oil. The resulting compositions were olfactorily compared with each other.

According to the perfumers, the addition of 2.5% by weight 4H-3,1-benzoxathiin 10% DPG gives the composition a uniqueness and special character. At the same time, glamorous aspects of white flowers complete the accord, which significantly increases in intensity.

Example of Embodiment 4

Perfume Oil Composition IV (Perfume Oil IV)

The following specified perfume oil can be used to perfume fabric softener.

TABLE 6

Composition of perfume oil composition IV:

| Odorant | Weight [mg] |
|---|---|
| ACETOACETIC ACID ETHYL ESTER | 8 |
| AGRUMEX LC | 10 |
| AMBERWOOD ® F | 14 |
| AMBRETTOLIDE | 2 |
| AMBROCENIDE ® CRYST. 1% DPG | 20 |
| AMBROXIDE 10% IPM | 5 |
| AURELIONE ® | 1 |
| BERGAMOTTOEL BERGAPTEN FREE | 1 |
| CASHMERAN | 12 |
| CEDARWOOD OIL VIRGINIA | 3 |
| CEDRAMBER | 10 |
| CEDROL KRIST. | 5 |
| CYCLOGALBANATE ® 1% DPG | 4 |
| DAMASCENON 10% TEC | 4 |
| DIMETHYL BENZYL CARBINYL ACETATE 10% IPM | 6 |
| DIPROPYLENE GLYCOL | 219 |
| ETHYLENE BRASSYLATE | 135 |
| ETHYLLINALOOL | 16 |
| FREESIOL/CORPS 119 | 10 |
| GALAXOLID PURE | 100 |
| GLOBALIDE ® | 10 |
| HEDION | 174 |
| HEXENYL ACETATE CIS-3 10% DPG | 3 |
| HEXENYL ISOBUTYRATE CIS-3 1% DPG | 6 |
| ISO E SUPER | 80 |
| KEPHALIS | 10 |
| LEAFOVERT ® 10% DPG | 6 |
| LINALYL ACETATE | 3 |
| MACROLIDE ® SUPRA | 16 |
| METHYLHEPTINE CARBONATE 1% DPG | 4 |
| NEO HELIOPAN ® OS | 43 |
| Neo Heliopan ® AV | 35 |
| Neo Heliopan ® BB | 8 |
| OCTALACTONE GAMMA 10% TEC | 6 |
| TIMBEROL ® | 4 |
| VERTOCITRAL 10% DPG | 7 |

The perfume oil prepared was divided into two equal parts. To exclude dilution effects, a first part of the perfume oil was mixed with 0.5% by weight of dipropylene glycol (DPG), based on the total amount of the first part of the perfume oil. To the second part of the perfume oil, 0.5% by weight of 2-methyl-4H-3,1-benzoxathiin 1% DPG was added (i.e., a 1% solution of 2-methyl-4H-3,1-benzoxathiin in DPG), based on the total amount of the part of the perfume oil. The resulting compositions were olfactorily compared with each other.

According to the perfumers, the composition gains fullness and character with the addition of 0.5% by weight of 2-methyl-4H-3,1-benzoxathiin 1% DPG. Opulent floral notes are highlighted and the accord is perceived much more intense.

Example of Embodiment 5

Perfume Oil Composition V (Perfume Oil V)

The following specified perfume oil can be used to perfume eau de toilettes.

TABLE 7

Composition of perfume oil composition V:

| Odorant | Weight [mg] |
|---|---|
| ALDEHYDE C14 SOG 10% DPG | 6 |
| ALDEHYDE C16 SOG. 10% DPG | 5 |
| BENZOIN SIAM CLAIR 50% DPG | 5 |
| BENZYL ACETATE | 280 |
| BENZYL PROPIONATE | 10 |
| DIPROPYLENE GLYCOL | 55 |
| EUGENOL NAT. | 15 |
| HEDION HC/70 | 240 |
| HEXENOL CIS-3 10% DPG | 10 |
| HEXENYL ACETATE CIS-3 10% DPG | 5 |
| HEXENYL BENZOATE CIS-3 | 40 |
| HEXYL CINNAMALDEHYDE ALPHA | 150 |
| ISOBUTYL-3-METHOXYPYRAZINE,2- 1 0.1% DEP | 5 |
| ISOEUGENOL ACETATE | 2 |
| JASMINLACTON | 5 |
| JASMON CIS | 2 |
| CRESOL PARA 10% DPG | 5 |
| LEAFOVERT ® 10% DPG | 5 |
| LINALOOL | 100 |
| MALTOLISOBUTYRATE 1% DPG | 10 |
| MAYOL 10% DPG | 5 |
| METHYL ANTHRANILATE 10% DPG | 10 |
| NECTARYL 10% DPG | 5 |
| VERTOMUGAL 10% DPG | 5 |
| YLANG YLANGOEL EXTRA FF 10% DPG | 5 |

The perfume oil prepared was divided into two equal parts. To exclude dilution effects, a first part of the perfume oil was mixed with 1.5% by weight of dipropylene glycol (DPG), based on the total amount of the first part of the perfume oil. To the second part of the perfume oil, 1.5% by weight of 2-methyl-4H-3,1-benzoxathiin 1% DPG was added (i.e., a 1% solution of 2-methyl-4H-3,1-benzoxathiin in DPG), based on the total amount of the part of the perfume oil. The resulting compositions were olfactorily compared with each other.

According to the perfumers, the addition of 1.5% by weight of 2-methyl-4H-3,1-benzoxathiin gives the composition a very animalic character, reminiscent of ylang-ylang and cresol. In addition, the addition creates a warm ambergris facet, accompanied by delicate florals and lactonic notes.

The invention claimed is:

1. A perfume oil, comprising an odorant or odorant mixture comprising a sensory effective amount of one or more compounds of formula (I)

Formula (I)

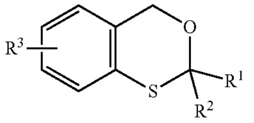

wherein $R^1$ represents H, a linear alkyl group $C_{1-2}$, a linear or branched alkyl group $C_{3-5}$, or a linear or branched alkenyl group $C_{1-5}$, $R^2$ represents H, a linear alkyl group $C_{1-2}$, a linear or branched alkyl group $C_{3-5}$ or a linear or branched alkenyl group $C_{1-5}$, and $R^3$ represents H, linear alkyl group $C_{1-2}$, or a linear or branched alkyl group $C_3$;

wherein the sum of the carbon atoms of $R^1$ and $R^2$ is not more than five carbon atoms; and wherein $R^3$ is located at one of the positions of the aromatic ring;

and their stereoisomers, diastereomers and enantiomers or mixtures thereof; and one or more additional odorants, wherein the one or more compounds of formula (I) are present at a concentration of 0.00001 to 1% by weight and impart an odor impression selected from floral, animalic, and leathery odor impressions.

2. The perfume oil of claim 1 wherein $R^1$ is not equal to $R^2$.

3. The perfume oil according to claim 1, wherein in each of the one or more compounds of formula (I), $R^2$ and $R^3$ are a hydrogen atom and wherein $R^1$ is H, a methyl, an isopropyl or tert-butyl group.

4. The perfume oil according to claim 1, wherein the one or more compounds of formula (I) are selected from one or more in the group of:

(i) 4H-3,1-benzoxathiin, (ii) 2-methyl-4H-3,1-benzoxathiin, and (iii) 2-isopropyl-4H-3,1-benzoxathiin.

5. The perfume oil of claim 1, wherein the perfume oil consists of the one or more compounds of formula (I) and the one or more additional odorants.

6. The perfume oil of claim 1, wherein the perfume oil is microencapsulated, spray-dried, an inclusion complex, or an extrusion product.

7. A perfume composition comprising the perfume oil according to claim 1, comprising and at least one carrier, and/or at least one formulation adjuvant and/or at least one functional agent.

8. A perfumed product selected from the group consisting of: detergents, hygiene products, personal care products, shampoos, and shower gels, comprising the perfume oil according to claim 1.

9. A method of using the perfume oil according to claim 1, comprising applying the perfume oil to a human body.

* * * * *